(12) United States Patent
Leggett et al.

(10) Patent No.: US 6,395,475 B1
(45) Date of Patent: *May 28, 2002

(54) SEMIAUTOMATED METHOD FOR FINGERPRINTING BACTERIAL DNA

(75) Inventors: Carol G. Leggett, Cairo, GA (US); Ellyn Whitehouse, Wacissa; Robert H. Reeves, Tallahassee, both of FL (US)

(73) Assignee: Florida State University

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/461,210

(22) Filed: Jun. 5, 1995

Related U.S. Application Data

(63) Continuation of application No. 08/064,596, filed on May 18, 1994, now abandoned.

(51) Int. Cl.$^7$ .......................... C12Q 1/68; C07H 21/02; C07H 21/04; C12N 15/00

(52) U.S. Cl. .......................... 435/6; 536/23.1; 536/24.3; 935/76; 935/77; 935/78

(58) Field of Search ....................... 435/91.2, 6; 436/63

(56) References Cited

U.S. PATENT DOCUMENTS

| 5,108,892 A | * | 4/1992 | Burke et al. | 435/6 |
| 5,298,392 A | * | 3/1994 | Atlas et al. | 435/600 |
| 5,753,467 A | * | 5/1998 | Jensen et al. | 435/91.2 |

FOREIGN PATENT DOCUMENTS

| WO | WO9215678 | 9/1992 |
| WO | PCT/US92/09230 | 4/1993 |
| WO | WO9311264 | 6/1993 |

OTHER PUBLICATIONS

Perkin–Elmer, BioTechnology Catalog (1992–1993) Amplitype HLA DQx Forensic DNA Amplification and Typing Kit, p. 26.*
Maniatis et al., Molecular Cloning a Laboratory Manual, 2nd Ed. (1989) Cold Spring Harbor Laboratory Press pp. 10.14–10.15.*
Bej et al., Amplification of Nucleic Acids by Polymerase Chain Reaction (PCR) and Other Methods and Their Applications (1991) Crit. Rev. Bioch. and Mol. Bio. 26:301–334.*
Voss et al. (1992) Methods in Mol. and Cell. Bio. 3:30–34.*
Barry et al. (1990) Bio/Technology 8: 232–236.*
Jensen et al. (Apr. 1993) Appl. & Environ. Micro. 59:945–952.*
Kronick et al. (1991) Clin. Chem. 37: 602.*
The Stratagene Catalog p.39 (1988).*
Conrad et al. Nucleic Acids Research 20(23) :pp.6423–6424 (1992).*
Landgraf et al. Analytical Biochemistry 193 (2) : pp.231–235 (1991).*
PCR Protocols Academic Press, Inc. Editors: Innis et al. (1990) pp.99–118.*
Chakrabarti, D. et al.: *Mol. & Biochem. Parasit.*, 52:75–84 (1992).
Liu, Y. et al.: *Nucleic Acids Res.*, 20(14):3763–3772 (1992).
Weiss, J.B. et al.: *Mol & Biochem. Parasit.*, 54:73–86 (1992).
Naito, E. et al.: *J. Forensic Sci., JFSCA*, 37(2):396–403 (Mar. 1992).
Hopkins, B. et al.: *Equine Vet. J.*, 23(4):277–279 (1991).
Knapp, M.R. et al.: *Int'l Soc. for Animal Genetics*, 23rd Conference of ISAG, pp. 6–7 (1992).
Kashi, Y. et al.: *Nucleic Acids Res.*, 18(5):1129–1132 (1990).
Nagy, M. et al.: *Vox Sang*, 61:59–61 (1991).
Haberfeld, A. et al.: *Animal Genetics*, 22:299–305 (1991).
Haley, C.S.: *Animal Genetics*, 22:259–277 (1991).
Buitkamp, J. et al.: *Animal Genetics*, 22:137–146 (1991).
Pinder, S.J. et al.: *Animal Genetics*, 22:11–20 (1991).
Janiszewska, J. et al.: *Genetica Polonica*, 31(2):137–143 (1990).
Kashi, Y. et al.: *J. Dairy Sci.*, 73:3306–3311 (1990).
Kasai, K. et al.: *J. Forensic Sci., JFSCA*, 35(5):1196–1200 (Sep. 1990).
Edwards, A. et al.: *Am. J. Hum. Genet.*, 49:746–756 (1991).
Moore, S.S. et al.: *Genomics*, 10:654–660 (1991).
Panaccio, M. et al.: *Biotechniques*, 14(2):238–242 (1993).
Patton, C.M. et al.: *J. Clin. Microbiol.*, 29(4):680–688 (Apr. 1991).
Mansfield, E.S. et al.: *Human Molecular Genetics*, 2(1):43–50 (1993).

(List continued on next page.)

Primary Examiner—Ethan C. Whisenant
(74) Attorney, Agent, or Firm—Akerman Senterfitt; Stanley A. Kim

(57) ABSTRACT

Methods and kits for typing prokaryotes and eukaryotes are disclosed. A specific DNA fragment in the rRNA intergene region is amplified by PCR using two universal oligonucleotide primers. The labeled PCR product is cleaved with a variety of restriction endonucleases and electrophoresed on an automated DNA sequencer. The methods and kits are beneficial in, for example, a clinical laboratory because they allow for rapid strain identification of pathogenic bacteria. The DNA fingerprinting methods and kits of the present invention are more definitive, since genomic bacterial DNA is used. One advantage of the methods of the present invention is the speed with which results are obtained. For example, a preliminary screen by agarose gel electrophoresis of a PCR product can be completed five to six hours after receiving hospital isolates. The preliminary screen can then be confirmed in approximately 24 hours by RFLP analysis on an automated sequencer. The speed of the methods of the present invention provide infection control personnel with adequate information to contain and prevent the spread of nosocomial infections, rather than having analyses done retrospectively.

4 Claims, 16 Drawing Sheets

OTHER PUBLICATIONS

Mayrand, P.E. et al.: *Applied and Theoretical Electrophoresis,* 3:1–11 (1992).
Ziegle, J.S. et al.: *Genomics,* 14(4):1026–1031 (Dec. 1992).
Brumfitt, W. et al.: *Dugs Exptl. Clin. Res.,* 16:205–214 (1990).
Zuccarelli, A. et al.: *J. Clin. Microbiol.,* 28(1):97–102 (Jan. 1990).
Tokue, Y. et al.: *Tohoku J. Exp. Med.,* 163:31–37 (1991).
Coia, J. et al.: *J. Med. Microbiol.,* 31:125–132 (1990).
Pennington, T. et al.: *J. Clin. Microbiol.,* 29:390–392 (1991).
Tveten, Y. et al.: *J. Clin. Microbiol.,* 29:110–1105 (1991).
Fluit, A. et al.: *Eur. J. Clin. Microbiol. Infect. Dis.,* 9:605–608 (1990).
Thomson–Carter, F. et al.: *J. Gen. Microbiol.,* 135:2093–2097 (1989).
Preheim, L. et al: *Eur. J. Clin. Microbiol. Infect. Dis.,* 10:428–436 (1991).
Applied Biosystems Brochure No. 236202, Genescan™ 672 Software Kit, Performance Specifications, pp. 1–6 (1994).
Bioventures, Inc.: GeneReleaser™ Protocol Revised Aug. 11, 1992 (for Research Use Only), pp. 1–3 (1992).
Bioventures, Inc.: Genereleaser PCR* Ready DNA In 10 Minutes, Example GeneReleaser™ Protocol (for Research Use Only), pp. 1–4 (1992).
Guevara, P. et al.: *Molecular and Biochemical Parasitology,* 56:15–26 (1992).
Bowles, J. et al.: *Molecular and Biochemical Parasitology,* 57:231–40 (1993).
Buchko, J. et al.: *Curr. Genet.,* 18:203–205 (1990).
Appels, R. et al.: *Can. J. Genet. Cytol.,* 28:665–672 (1986).
Kwan, H.–S. et al.: *Experimental Mycology,* 16:163–166 (1992).
Henriques, M. et al.: *Yeast,* 7:167–172 (1991).
Murthy, V.K. et al.: *Molecular and Cellular Probes,* 6:237–243 (1992).
Cai, J. et al.: *Biochemica et Biophysica Acta.,* 1131:317–320 (1992).
Mills, P.R. et al.: *FEMS Microbiology Letters,* 98:137–144 (1992).
Cox, A.V. et al.: *Theor Appl Genet,* 83:684–690 (1992).
Gardes, M. et al.: *Can. J. Bot,* 69:180–190 (1991).
Orias, E. et al.: *J. Protozool.,* 38(4):306–311 (Jul.–Aug. 1991).
Moukhamedov, R. et al.: *Phytopathology,* 84(3) :256–259 (1994).

* cited by examiner

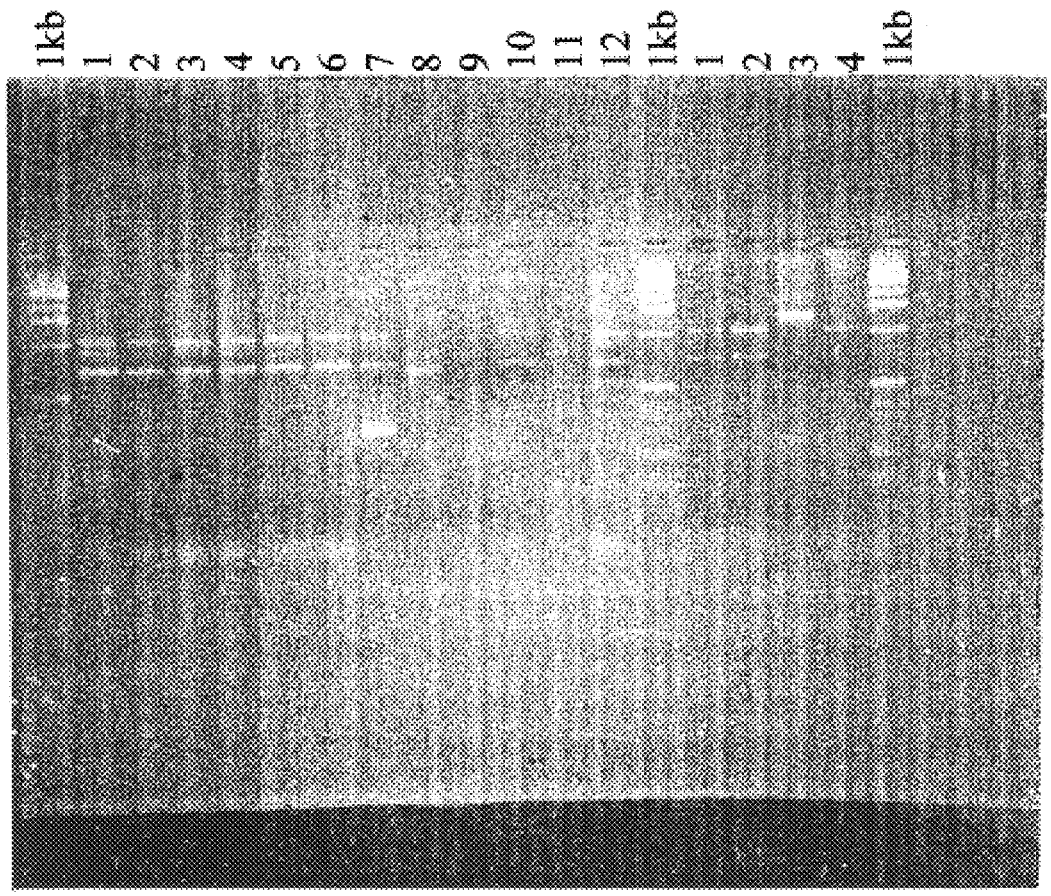

PCR#64 & 65  2%Gel

2% agarose gel of several eukaryote amplified with primers C-C and 7.
Contents of the lanes are as follows:

1 kb ladder
1. Horse (Sun's Remembrance; TWH* stallion)
2. Horse (Widow's Tar Baby; TWH* mare)
3. Horse (Sun's Sweet Celebration; TWH* filly)     *TWH = Tennessee Walking Hors
4. Horse (Daybreak Darling; App mare)     APP = Appaloosa
5. Horse (Pokey's Fawn; App** mare)
6. Horse (Bojangles; grade pony)
7. Amphioxus (primitive worm)
8. Cockroach (insect)
9. Mouse (mammal; did not amplify in this particular experiment)
10. Avian (Rose Breasted Cockatoo)
11. no sample loaded
12. Salamander (amphibian)
    1 kb ladder
1. Human
2. Human
3. Sea Urchin (echinoderm)
4. Rabbit (mammal)

FIG. 4

```
              ETS1       18S      5.8S            28S           ETS2
Eukaryotic: ========|========|==|==|==|====================|===
                            ITS1      ITS2
```

```
              16S             23S      5S
Prokaryotic:  ====|======|==|============|=|==
                       IGR1           IGR2
```

*FIG. 10*

| Peak/Lane | Min. | Size | Peak Height | Peak Area | Scan # |
|---|---|---|---|---|---|
| 1B, 21 | 348 | 275.82 | 1699 | 21223 | 3485 |
| 2B, 21 | 351 | 278.42 | 2097 | 42544 | 3515 |
| 3B, 21 | 356 | 282.51 | 2836 | 64635 | 3562 |
| 4B, 21 | 374 | 298.80 | 5018 | 81844 | 3747 |
| 5B, 21 | 456 | 372.08 | 220 | 2949 | 4560 |
| 6B, 21 | 492 | 404.62 | 3206 | 23801 | 4920 |
| 7B, 21 | 492 | 405.37 | 3459 | 90500 | 4928 |
| 8B, 21 | 569 | 483.90 | 509 | 11467 | 5692 |
| 9B, 21 | 598 | 517.96 | 637 | 16232 | 5989 |
| 10B, 21 | 620 | 535.97 | 264 | 4775 | 6205 |
| 11B, 21 | 633 | 548.62 | 240 | 3512 | 6333 |

■ Lane 4: PCR35 S#5 Hha I

Gel File: Clinical Gel

| Peak/Lane | Min. | Size | Peak Height | Peak Area | Scan # |
|---|---|---|---|---|---|
| 1B, 4 | 145 | 96.69 | 338 | 2201 | 1454 |
| 2B, 4 | 212 | 157.15 | 279 | 2370 | 2129 |
| 3B, 4 | 318 | 253.34 | 434 | 4505 | 3187 |
| 4B, 4 | 319 | 254.37 | 478 | 5146 | 3199 |
| 5B, 4 | 320 | 255.22 | 324 | 3739 | 3209 |
| 6B, 4 | 344 | 275.82 | 1203 | 15240 | 3449 |
| 7B, 4 | 348 | 278.67 | 2544 | 37089 | 3481 |
| 8B, 4 | 352 | 282.60 | 5895 | 79477 | 3525 |
| 9B, 4 | 370 | 298.83 | 2867 | 45613 | 3707 |
| 10B, 4 | 487 | 405.37 | 1186 | 20164 | 4873 |
| 11B, 4 | 550 | 469.35 | 285 | 2427 | 5501 |
| 12B, 4 | 561 | 482.98 | 2335 | 44437 | 5617 |
| 13B, 4 | 590 | 519.26 | 2503 | 51254 | 5909 |
| 14B, 4 | 611 | 537.12 | 1502 | 26597 | 6119 |

Lane 19: PCR35 S#8 Hind III

Gel File: Clinical Gel

| Peak/Lane | Min. | Size | Peak Height | Peak Area | Scan # |
|---|---|---|---|---|---|
| 1B, 19 | 127 | 79.94 | 329 | 1639 | 1273 |
| 2B, 19 | 146 | 96.59 | 438 | 2607 | 1467 |
| 3B, 19 | 321 | 253.26 | 283 | 2771 | 3219 |
| 4B, 19 | 323 | 254.36 | 319 | 3759 | 3232 |
| 5B, 19 | 324 | 255.29 | 232 | 2895 | 3243 |
| 6B, 19 | 422 | 341.41 | 218 | 2001 | 4224 |
| 7B, 19 | 423 | 342.51 | 358 | 3874 | 4236 |
| 8B, 19 | 424 | 343.32 | 401 | 7154 | 4245 |
| 9B, 19 | 426 | 345.33 | 265 | 4864 | 4267 |
| 10B, 19 | 442 | 359.62 | 384 | 8243 | 4423 |
| 11B, 19 | 461 | 377.06 | 360 | 4229 | 4619 |
| 12B, 19 | 462 | 377.60 | 359 | 7497 | 4625 |
| 13B, 19 | 470 | 384.77 | 298 | 9712 | 4704 |
| 14B, 19 | 524 | 436.91 | 458 | 6076 | 5248 |
| 15B, 19 | 526 | 439.02 | 4018 | 104570 | 5269 |
| 16B, 19 | 540 | 452.73 | 397 | 3459 | 5403 |
| 17B, 19 | 542 | 454.60 | 3914 | 112297 | 5421 |
| 18B, 19 | 549 | 462.14 | 277 | 4456 | 5493 |
| 19B, 19 | 551 | 464.57 | 382 | 4345 | 5516 |
| 20B, 19 | 552 | 465.52 | 496 | 12176 | 5525 |
| 21B, 19 | 555 | 469.14 | 1422 | 14751 | 5559 |
| 22B, 19 | 558 | 472.41 | 3461 | 107263 | 5588 |
| 23B, 19 | 566 | 480.85 | 321 | 9223 | 5661 |
| 24B, 19 | 573 | 489.53 | 257 | 2220 | 5735 |
| 25B, 19 | 625 | 542.57 | 4033 | 35310 | 6253 |
| 26B, 19 | 626 | 543.58 | 4327 | 68476 | 6263 |
| 27B, 19 | 628 | 545.98 | 4057 | 88251 | 6287 |

Lane 17: PCR35 S#6 Hind III

Gel File: Clinical Gel

| Peak/Lane | Min. | Size | Peak Height | Peak Area | Scan # |
|---|---|---|---|---|---|
| 1B, 17 | 146 | 96.56 | 366 | 2140 | 1462 |
| 2B, 17 | 217 | 160.14 | 273 | 2460 | 2173 |
| 3B, 17 | 320 | 253.37 | 224 | 2084 | 3206 |
| 4B, 17 | 321 | 254.39 | 268 | 2835 | 3218 |
| 5B, 17 | 440 | 359.60 | 263 | 2550 | 4403 |
| 6B, 17 | 459 | 376.49 | 335 | 3861 | 4595 |
| 7B, 17 | 460 | 377.47 | 348 | 5811 | 4606 |
| 8B, 17 | 478 | 394.05 | 611 | 6257 | 4789 |
| 9B, 17 | 481 | 396.82 | 4354 | 93558 | 4819 |
| 10B, 17 | 497 | 411.69 | 1599 | 16552 | 4977 |
| 11B, 17 | 499 | 413.79 | 5671 | 58957 | 4999 |
| 12B, 17 | 500 | 414.47 | 5853 | 141593 | 5006 |
| 13B, 17 | 550 | 464.74 | 325 | 7927 | 5503 |
| 14B, 17 | 554 | 469.25 | 439 | 4951 | 5545 |
| 15B, 17 | 580 | 499.73 | 811 | 8855 | 5801 |

SEMIAUTOMATED METHOD FOR FINGER-PRINTING BACTERIAL DNA

This is a continuation of Ser. No. 08/064,596 filed on May 18, 1994 now abandoned.

BACKGROUND

Nosocomial (hospital-based) infections have become one of the most serious problems in infectious disease. *Staphylococcus aureus* is exceeded only by *Escherichia coli* as a leading cause of nosocomial infections. See, for example, Brumfitt, W. et al., *Drugs Exptl. Clin. Res.*, 16:205–214 (1990). One type of *S. aureus*, methicillin-resistant *S. aureus* (MRSA), is of a particular interest because it is resistant to all penicillin-based antibiotics.

Patients in the intensive care unit are very susceptible to bacterial infections, due to interventions such as respiratory tubes and indwelling catheters. *E. coli* and *S. aureus*, if introduced into surgical wounds, the blood stream or the urinary tract, cause serious, sometimes life-threatening infections. The Infection Control Committees of most hospitals are constantly fighting this problem. There is no easy solution to the problem, but a partial solution in most "nosocomial outbreaks" is simply identifying the source of the infection. That is, is the infectious agent coming from a common source (e.g. an infected nurse or doctor, or an instrument such as a respirator) or is there some other reason for the sudden emergence of a single type of bacterial infection.

Hospital laboratories can quickly identify the infectious agent (e.g., *S. aureus*), but they do not have the ability to determine whether a single strain of the organism is causing the outbreak (and therefore a possible common source) or if several different strains are responsible for the outbreak. At the present time most of these outbreaks can only be characterized in retrospect, since the outbreak is over before the bacterial isolates can be identified. For example, in an outbreak of *S. aureus* in a hospital nursery, the isolates can be identified in a matter of 1 or 2 days, but the strain identification usually takes weeks or even months, because the strains are still analyzed by slow culture-based methods which are labor intensive.

Current methods of strain typing bacteria include phage typing, plasmid analysis, and antibiotic susceptibility (biotyping). See, for example, Zuccarelli, A. et al.: *J. Clin. Microbiol.*, 28:97–102 (1990); Tokue, Y. et al.: *Tohokin J. Exp. Med.*, 163:31–37 (1991); Coia, J. et al.: *J. Med. Microbiol.*, 31:125–132 (1990); Pennington, T. et al.:*J. Clin. Microbiol.*, 29:390–392 (1991); Tveten, Y. et al.: *J. Clin. Microbiol.*, 29:110–1105 (1991); Fluit, A. et al.: *Eur. J. Clin. Microbiol. Infect. Dis.*, 9:605–608 (1990); Thomson-Carter, F. et al.: *J. Gen. Microbiol.*, 135:2093–2097 (1989); and Preheim, L. et al.: *Eur. J. Clin. Microbiol. Infect. Dis.*, 10:428–436 (1991). These methods, currently used by the Centers for Disease Control, are laborious, time consuming (approximately one month) and often yield inconclusive results.

Consequently, there is a serious need in the medical community for means to not only identify the infectious agents, but also to rapidly characterize the strain or strains involved so that effective measures may be timely employed.

SUMMARY OF THE PRESENT INVENTION

In brief, the present invention alleviates and overcomes certain of the above-mentioned drawbacks of the present state of the art through the discovery of novel methods and kits for rapidly fingerprinting DNA to identify prokaryotic and eukaryotic species, subspecies, and especially strains or individuals of the subspecies. As to prokaryotic organisms, the present invention is especially suited for identifying different bacterial strains involved in, for example, nosocomial infections, since the methods and kits are believed to be sensitive enough to detect differences between, for example, bacterial isolates of the same species. With respect to eukaryotes, the present invention contemplates identifying, for instance, species, subspecies, and the differences between the individuals of the subspecies, such as pedigrees.

Generally speaking, the present invention involves the use of polymerase chain reaction (PCR) technology and restriction fragment length polymorphism analysis of genomic DNA preferably containing numerous gene clusters, such as ribosomal RNA (rRNA) gene clusters. In accordance with the present invention, a specific DNA fragment in a gene cluster region, such as the rRNA intergene region, is amplified by PCR using two universal oligonucleotide primers. This area of the genome is generally ideal for such a procedure because a highly variable spacer region is flanked by two highly conserved genes which may be used as primer sites. Before PCR amplification, however, the oligonucleotides are preferably fluorescently labeled. While it is preferable to label the 5' end primers, the 3' end primers or both the 5' and 3' end primers, as well as the individual nucleotides utilized during PCR may be labeled. Because the 5' end of each cluster is preferably flourescently-labelled, each fragment is represented as an individual peak on a waveform pattern. Therefore, since *E. coli* has seven clusters within its genome, multiple peaks will be present on the waveform pattern. The labeled PCR product may then be cleaved with a variety of restriction endonucleases and electrophoresed on an automated DNA sequencer.

Thus, the methods and kits of the present invention generally depend upon rapid, semiautomated DNA analysis, and more particularly, upon a type of DNA fingerprinting of multiple segments of DNA, such as the ribosomal RNA gene clusters, that are common to particular prokaryotic or eukaryotic species. Morover, the methods and kits are believed to be most beneficial in a clinical laboratory because they allow for rapid strain identification of pathogenic bacteria. The DNA fingerprinting methods and kits of the present invention are also believed to be more definitive than currently practiced methodologies, since genomic DNA is used.

One main advantage of the methods and kits of the present invention is the speed with which results are obtained. A preliminary screen by agarose gel electrophoresis of a PCR product can be completed within five to six hours after receiving a sample, such as a hospital isolate. More particularly, the differences in the intergene region are detected on, for example, a 2% agarose gel, by banding patterns following PCR. Identical strains will exhibit similar banding patterns, whereas strains from other sources or of different types will differ in band intensity and fragment size (as demonstrated in FIG. 1).

The preliminary screen can then be confirmed in approximately 24 hours by restriction fragment length polymorphism (RFLP) analysis on an automated sequencer. For example, more definitive analyses are performed on the Applied Biosystems, Inc. (Foster City, Calif.) vertical electrophoresis unit with the Genescan software. Following PCR, restriction endonuclease digestions are performed and the cleaved fragments are loaded directly onto the electrophoresis unit. Although a multitude of restriction endonucleases are available for performing this assay, HhaI and HindIII are believed to be the most informative concerning at least prokaryote typing.

MRSA digested with HhaI consistently exhibit patterns with fragment lengths of 276, 278, 283, and 299 base pairs (see FIG. 2). Although fragment sizes are consistent among strains, a remarkable difference in band intensity is noted for each individual strain. Band intensity is measured by the software as peak area and may be converted to gene dosage (gene copy number) by using a reference gene during the electrophoresis run. It is our belief that differences between strains or individuals of subspecies may be determined based on gene dosage of each fragment at these given positions. A gene which may be universal among eubacteria and may be useful as a standard gene for calculating gene dosages has also been identified. This gene is dna A.

HindIII restriction endonuclease digestions of MRSA have been used to corroborate HhaI data. Typical HindIII patterns exhibit two to three fragment groupings with varying fragment lengths (see FIG. 3). Each grouping is typically positioned fourteen to twenty bases away from its neighboring group. Strain determinations are based on the number of groupings present and fragment length. The speed of these procedures provides, for example, infection control personnel adequate information to contain and prevent the spread of nosocomial infections, rather than having analyses done retrospectively.

Accordingly, it can now be appreciated that the present invention is believed to provide a solution to identifying differences between species, subspecies, and strains of prokaryotic organisms and individuals of subspecies of higher life forms.

The above features and advantages will be better understood with reference to the FIGS., Examples, and Detailed Description set out herein below. It will also be understood that the methods and kits of the present invention are exemplary only and are not to be regarded as limitations of this invention.

BRIEF DESCRIPTION OF THE FIGS.

Reference is now made to the accompanying FIGS. in which are shown characteristics corresponding to the unique DNA fingerprinting data generated via the methods of the present invention from which certain of their novel features and advantages will be apparent:

FIG. 1 is a preliminary screen of amplified intergene regions of clinical MRSA isolates. PCR products were electrophoresed on a 2% agarose gel and stained with ethidium bromide. Lanes 1 and 2, isolate A; lanes 3 and 4, isolate B; lanes 5 and 6, isolate C.

FIG. 4 is a preliminary screen of amplified intergene regions of higher life forms. PCR products were electrophoresed on a 2% agarose gel and stained with ethidium bromide.

FIG. 10 is an organization of typical eukaryotic and prokaryotic rRNA gene clusters;

DETAILED DESCRIPTION

Figure 1:
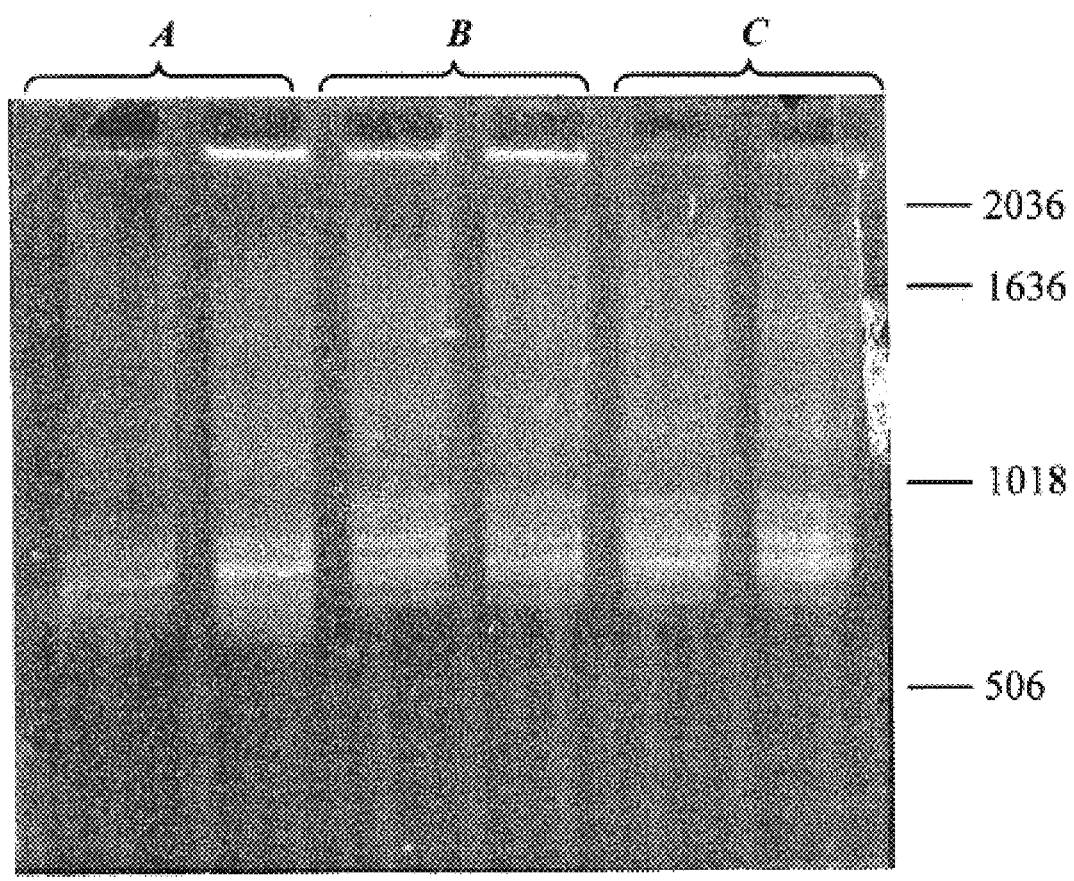
Figure 2:
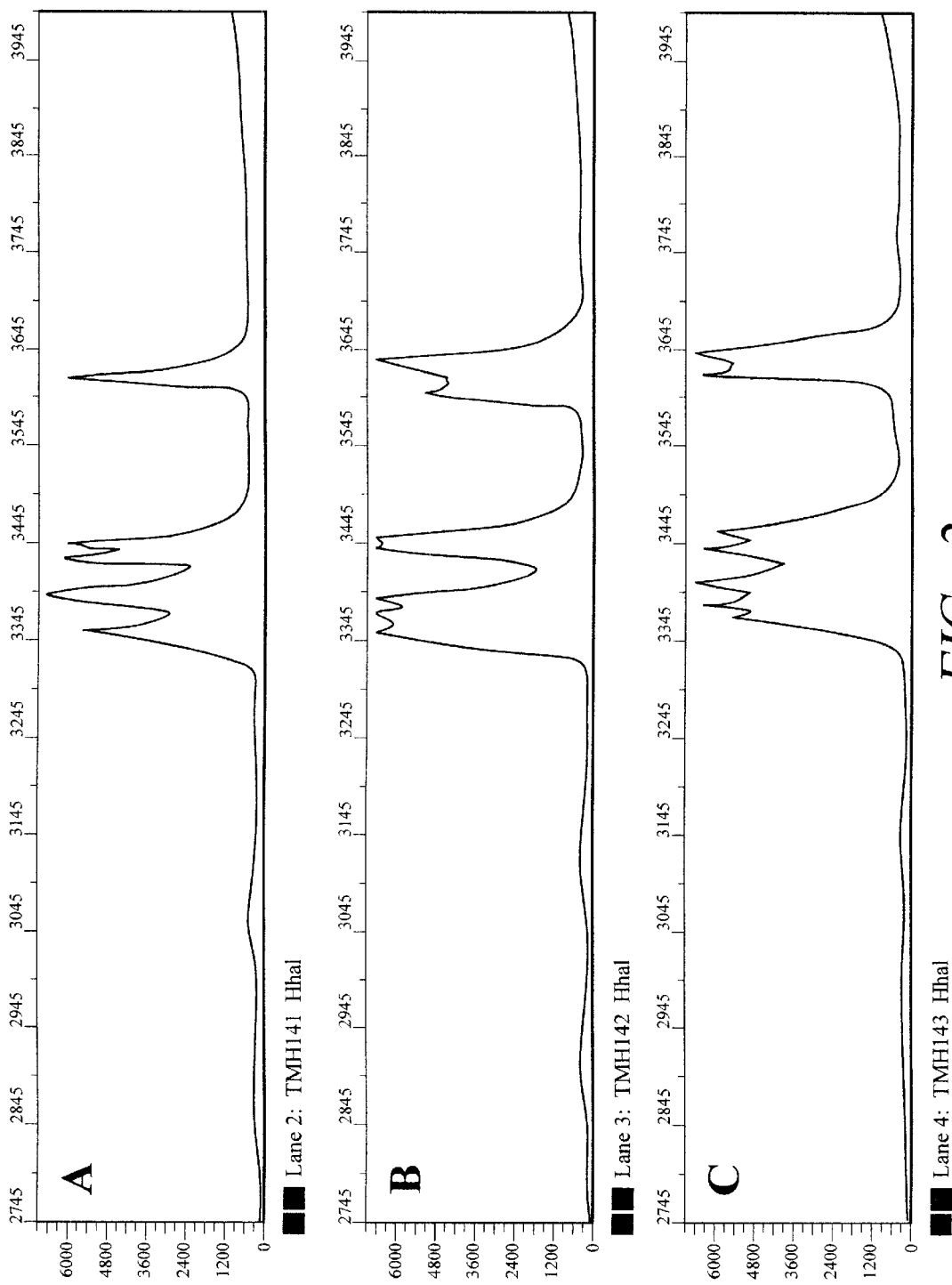
FIG. 2 is a comparison of electrophoretograms of the amplified intergene region of three clinical isolates cleaved with HhaI. Similarities between isolates B and C indicate they are from a common source, whereas isolate A originates from an independent source.
Figure 3:
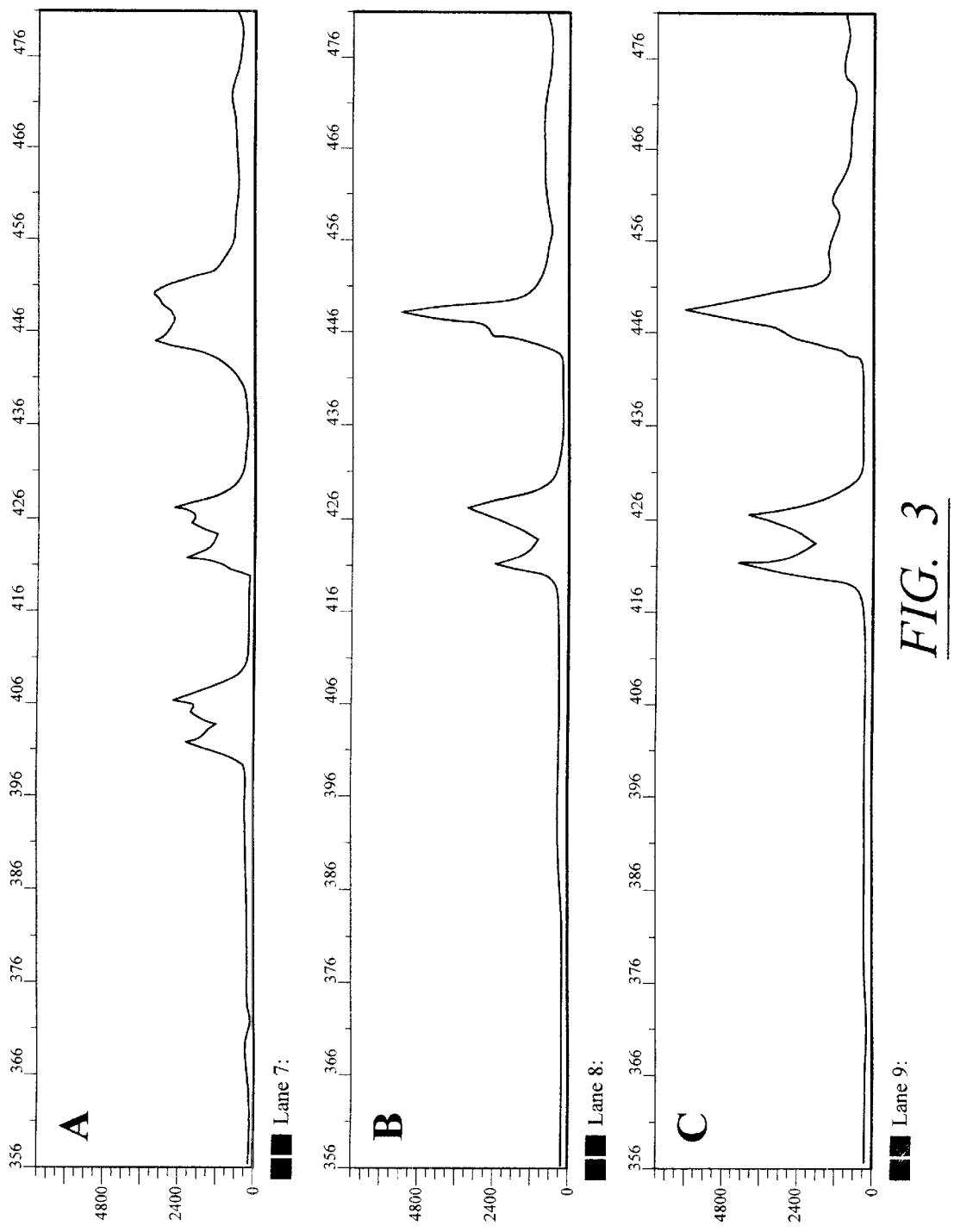
FIG. 3 is a comparison of electrophoretograms of the amplified intergene region of three clinical isolates cleaved with HindIII. Similarities between isolates B and C indicate they are from a common source, whereas isolate A originates from an independent source.

By way of illustrating and providing a more complete appreciation of the present invention and many of the attendant advantages thereof, the following detailed description is provided concerning the novel methods and kits.

The present invention provides methods and kits for DNA fingerprinting to determine similarities and/or differences between strains or individuals of subspecies. More particularly, the methods involve a rapid, semi-automated method for identifying strains of prokaryotic organisms or individuals of higher life forms and differences therebetween. More specifically, a specific DNA fragment in the rRNA intergene region is amplified by PCR using two universal oligonucleotides. While it has been realized that this area of the genome, i.e., the rRNA intergene region, is ideal for such a procedure because a highly variable spacer region of DNA is flanked by two highly conserved genes which may be used as primer sites, any area of the genome of any prokaryotic or eukaryotic life form may be selected, so long as it too contains a highly variable spacer region of DNA flanked by two highly conserved genes that may be used as primer sites for PCR amplification.

It should also be understood that any suitable oligonucleotide may serve as a primer. While a list of exemplary primers are recited in Table I, it should be understood that their complementary sequences may likewise be employed. It should also be understood that primers designated as CC and 7 in Table I are preferred and that they may be employed with those prokaryotes identified in Table II.

Exemplary of primers that may be used in accordance with this invention include those recited in Table I and the complementary sequences thereto (not listed).

TABLE I

PRIMERS 16S rRNA GENE

|  | | |
|---|---|---|
|  | SEQ ID NO:1: | AGA GTT TGA TCA TGG CTC |
| F₂C | SEQ ID NO:2: | CGA GTT TGA TCC TGG CTC |
| A-C | SEQ ID NO:3: | CAG CCG CGG TAA TAC |
| G-C | SEQ ID NO:4: | AAC AGG ATT AGA TAC CCT GG |
| B-C | SEQ ID NO:5: | CAA AGG AAT TGA CGG |
| H-C | SEQ ID NO:6: | TGG CTG TCG TCA GCT CGT GT |
| E-C | SEQ ID NO:7: | GAC GTC AAG TCA TCA |
| C-C | SEQ ID NO:8: | GTA CAC ACC GCC CGT |
| T-C | SEQ ID NO:9: | AAG TCG TAA CAA GGT |
| D-C | SEQ ID NO:10: | ATT AGC TAG TAG GTG |

23S rRNA GENE

|  | | |
|---|---|---|
| 7 | SEQ ID NO:11: | TCG CTC GCC GCT ACT |
| 8 | SEQ ID NO:12: | AGG GCA TCC ACC GTG |
| 9 | SEQ ID NO:13: | ACT GGT TCA CTA TCG |
| 10 | SEQ ID NO:14: | TCG GGG AGA ACC AGC TA |
| 11 | SEQ ID NO:15: | CCA GTG AGC TAT TAC GC |
| 12 | SEQ ID NO:16: | AGG AAT ATT AAC CTG TT |
| 13 | SEQ ID NO:17: | CCA CCC TCT GTG TCG GGT TT |
| 14 | SEQ ID NO:18: | ATT TCG CTA CCT TAG |
| 15 | SEQ ID NO:19: | TTT TAT CCG TTG AGC GA |
| 16 | SEQ ID NO:20: | CTT AGA TGC TTT CAG C |
| 17 | SEQ ID NO:21: | TGA CCC ATT ATA CAA AAG GT |

5S Oligonucleotide 5equences

|  | | |
|---|---|---|
| #15 5S | SEQ ID NO:22: | CCC ATG GGC AAC TCA |
|  | SEQ ID NO:23: | CCC ATT GGC AAC TCA |
|  | SEQ ID NO:24: | CCC ATA GGC AAC TCA |
|  | SEQ ID NO:25: | CCC ATC GGC AAC TCA |
| #323 5S-C | SEQ ID NO:26: | TGA GTT CGG GAT GGG |
|  | SEQ ID NO:27: | TGA GTT CGG TAT GGG |
|  | SEQ ID NO:28: | TGA GTT CGG AAT GGG |
|  | SEQ ID NO:29: | TGA GTT CGG CAT GGG |
| #810 5Srev | SEQ ID NO:30: | CTG TGT TCG GCA TGG |
|  | SEQ ID NO:31: | CTG TGT TCG ACA TGG |

TABLE II

Confirmed Prokaryotic Genera Which Contain
Both C-C and 7 Primer Sequences

Gram Negative Gamma Proteobacteria:

Shigella sp.
Escherichia sp.
Salmonella sp.
Klebsiella sp.
Enterobacter sp.
Citrobacter sp.
Proteus sp.
Hafnia sp.
Providencia sp.
Serratia sp.
Yersinia sp.
Vibrio sp.
Xanthomonas sp.

Gram Negative Beta Proteobacteria:

Commomonas sp.

Low GC Content Grain Positive Genera:

Bacillus sp.
Staphylococcus sp.
Streptococcus sp.

High GC Content Gram Positive Genera:

Arthrobacter sp.
Terrabacter sp.
Cyanobacterium Genera

In carrying out the methods of the present invention, the amplified product is preferably labeled during or prior to amplification. This may be accomplished by using one 5' end labeled primer from the 16S gene for prokaryotic typing. Several other options, however, may be employed. For example, 1.) a 5' end labeled primer may be employed from the 23S gene or 5S gene, 2.) 5'-end-labeled primers may be employed from the 16S and 23S or 23S and 5S or 16S and 5S genes, 3.) both primers may be employed in conjunction with fluorescently labeled dioxynucleotide triphosphate (dNTPs), or 4.) labeled dNTPs may be employed alone in the PCR reaction. With respect to eurokaryotic typing, similar combinations may be used, but for the eukaryotic structural genes, i.e., 18S or 5.8S or 28S, or 18S and 5.8S, or 5.8S and 28S, or 18S and 28S. In either prokaryotic or eukaryotic typing, it should be understood that labeling may be accomplished by using both 5' end labeled primers in conjunction with fluorescently labeled deoxynucleotide tryphosphates (dNTPs) or by using the labeled dNTPs alone in the PCR reaction.

It should be further appreciated that while amplification of the highly variable spacer region between the 16S and 23S genes is preferred, the methods of the present invention contemplate amplifying highly variable spacer regions between the 23S and 5S genes in prokaryotes and the highly variable spacer regions between the 18S and 5.8S and the 5.8S and 28S genes in eukaryotes. Of course, the present invention contemplates amplifying any highly variable spacer region of DNA or RNA which lies between two highly conserved DNA or RNA regions, respectively.

To type prokaryotes, such as bacterial strains, clinical isolates are sent from a hospital (or other source) on agar slants. Multiple colonies (4–5) are collected on a loop and resuspended in 50 μl 10 mM EDTA in a microcentrifuge tube. The tube is boiled for five minutes and the resultant lysate, containing the DNA template, is used in a polymerase chain reaction (PCR).

PCR is prepared using 10 μl of a 10× Taq Amplification Buffer (50 μl 1 M Tris-HCl, pH 8.3; 250 μl 1 M KCl; 20 μl 1 M $MgCl_2$; 2.25 μl NP-40; 2.25 μl Tween 20; 5 μl 1% gelatin; and 170.5 μl distilled water), 4 μl 2.5 mM dNTP mix (2.5 mM each dATP, dCTP, dGTP, dTTP), 100 ng fluorescently labeled 16S rRNA primer SEQ ID NO:8: (GTA CAC ACC GCC CGT), 100 ng nonlabeled 23S rRNA primer SEQ ID NO:11: (TCG CTC GCC GCT ACT), 1–10 μl of lysate from whole cells, 2.5 units AmpliTaq DNA polymerase, and sterile distilled water to bring the total volume to 100 μl. This mixture is overlayed with 100 μl mineral oil and placed in a Thermal Cycler (Perkin-Elmer, Norwalk, Conn.) under the following reaction conditions: 5 minute delay at 95° C., 35 cycles at 95° C. for 40 seconds, 50° C. for 25 seconds, 72° C. for 3 minutes; 10 minute delay at 72° C., followed by a 4° C. soak.

The PCR mixture is then separated from the oil overlay and 8 μl of the aqueous phase is mixed with 2 μl of a standard gel loading buffer. The aliquot is electrophoresed on a 2% agarose gel at 70 volts for one to two hours. The gel is stained with ethidium bromide and viewed under U-V illumination. The banding pattern reflects the rRNA gene cluster number of each bacterium. This initial pattern can be used as a preliminary test to distinguish between bacterial strains. If the banding patterns are very similar and more definitive results are desired, then a fingerprint is done on an automated sequencer.

The PCR mixture is passed through a G-50 column to remove unincorporated dNTPs and primers. The DNA concentration is determined on a minifluorometer. The PCR mixture then undergoes a 2-hour restriction digest with various four of six base endonucleases. An aliquot of the restriction digests is loaded onto a 6% polyacrylamide gel and electrophoresed on the 373A DNA Sequencing System (Applied Biosystems, Inc., Foster City, Calif.). The resulting DNA fingerprint is preserved in a gel file and can be printed onto paper as waveform patterns. See waveform FIGS. GeneScan software, which has been introduced by ABI, should enable the determination of DNA fragment size and gene dosage.

The Genescan software automates DNA fragment analysis by using an internal lane size standard on either an agarose or polyacrylamide gel to determine DNA fragment size and quantity. The software is used with either the 373A Electrophoresis unit (Applied Biosystems, Inc., Foster City, Calif.) or with the ABI horizontal gel unit (Gene Scanner 362 Fluroescent Fragment Analyzer). Both electrophoresis units use an argon laser to excite fluorescent dyes which have been attached to the DNA molecules. The fluorescence emission is detected by a photomultiplier tube which converts the light signal to a digitized signal. The data are collected in real time on a Macintosh computer.

This technology allows to quantitatively analyze DNA fragments in just a few hours, as opposed to the lengthy turnaround time associated with the traditional methods of Southern hybridizations and Dot Blots. Moreover, these traditional protocols generally require a week to complete and are labor-intensive. In addition, radiolabeled nucleotides must be used during analysis.

In general, procedures for certain aspects of the methods of the present invention are similar to that followed for automated sequencing. A 6% polyacrylamide gel is prepared and the gel is cast with a 24- or 36-well comb specifically designed for use with the Genescan software. DNA which has been 5' end labeled and digested with a restriction endonuclease is dried in a Speedvac concentrator (Savant), resuspended in a mix of 4 μl deionized formamide and 0.5 μl internal lane size standard (GENESCAN-2500 ROX or FAM), and is loaded onto the gel. The 24 cm well to read gel is electrophoresed, for example, for 14 hours in TBE buffer under a constant current of 2500 volts.

Fragment analysis is carried out with the matrix configuration determined for standard DYEDEOXY™ Terminator sequencing reactions or with a custom matrix. The matrix is used in the algorithms which calculate DNA mobility through the gel. Essentially, a waveform pattern (electrophoretogram) and tabular data are generated for each sample loaded. The electrophoretogram is a record of the banding pattern within the gel. Signal intensity follows a baseline value until a band is distinguished. A peak is present on the electrophoretogram for that DNA sample.

Tabular data are also generated for each sample. These data are presented in a spreadsheet format and given numerical value to each DNA band detected. Each band (peak) is numbered and the time at which that peak was detected is recorded. The size of each band is calculated according to the internal lane size standard. Although several methods are available for determination of fragment size, the Local Southern method is used because fragments generally in the 50 to 400 basepair range are analyzed. It is believed that this method creates a best-fit line through all the available points and then uses values on that line to calculate fragment values. Peak height and peak area are also included in the tabular data. These values, particularly peak area, are important in quantitating DNA samples and in determining gene dosage.

Because several fluorescent dyes are detected on either of the electrophoresis units currently sold by ABI, four different labels may be used to analyze DNA fragments within one lane on the gel. The number of samples analyzed on each gel may be increased, which therefore increases throughput by a factor of three or four. In one instance, it may be preferred to analyze a sample using three different restriction endonucleases. Therefore, a labeled 16S primer, for example, would be used in the three different digests but with a different colored label associated with each particular digest; perhaps blue with HhaI, yellow with HindIII, and green with TaqI. Following the restriction digest, the samples would be combined and loaded onto the gel. A multicolored banding pattern would result and would ultimately provide a very specific fingerprint for that particularly isolate. This ability also allows for a large number of samples in a short period of time. For example, up to 96 restriction patterns could be determined on one gel run with 24 lane run or 144 patterns on a 36 lane gel.

ABI is believed to be currently creating an upgrade which would permit gel runs as short as one to two hours. With this upgrade, two to three gels could be run within an eight hour work day and an additional gel could be run overnight. A laboratory remaining open for 24 hours could conceivably process ten to twelve gels a day per instrument. Therefore, 700 to 1100 fingerprints could be generated every 24 hours per instrument.

In eukaryotic cells, the ribosomal RNA (rRNA) genes are organized somewhat differently than in prokaryotic (bacterial) cells. Most notably the 5S genes, which are closely linked to (and transcribed with) the other rRNA genes in bacteria, are separated from the 18S and the 28S rRNA genes in eukaryotic cells. In addition the ribosomes of eukaryotic cells contain an extra small RNA, the 5.8S RNA which has been shown to be homologous to the 5'-end of the bacterial 23S RNA. The 5.8S gene is located just in front of (on the 5'-side of) the 28S gene. Shown below in FIG. 10 is the organization of a typical eukaryotic rRNA gene cluster. It is compared to the homologous cluster of rRNA genes observed in almost all bacteria.

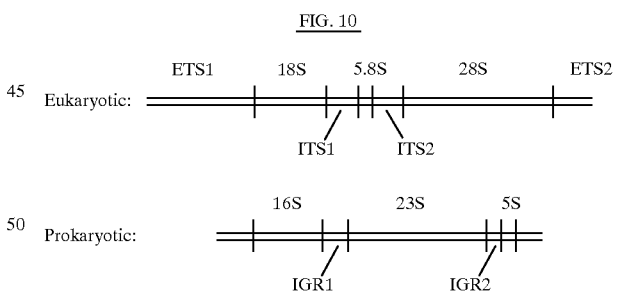

FIG. 10

The prokaryotic rRNA gene cluster (rrn) is composed of the 16S RNA gene followed by the 23S and 5S genes. The two IGRs are highly variable interGene regions between the three structural genes. They are transcribed with the genes to give a precursor RNA of about 5200 nucleotides, but are removed by ribonuclease cutting of the total transcript. A promoter of transcription is located just before the 16S gene and a transcriptional terminator is located just beyond the 5S gene.

In eukaryotes a much larger initial transcript is made— typically about 13,000 nucleotides long. Before the 18S gene is ETS1, the first external transcribed spacer. A second external spacer is located just beyond the 28S gene. Two highly variable internal transcribed spacers, ITS1 and ITS2, are located between the 18S and 5.8S and between the 5.8S and 28S genes, respectively. There are approximately 2300 nucleotides in the 18S RNA, 160 nucleotides in the 5.8S RNA and some 4200 nucleotides in the 28S RNA. In all eukaryotes multiple copies of this rRNA gene cluster are found in the nucleolus, and there may be several nucleoli inside the nucleus of a single cell. In the cnucleolus the rRNAs are transcribed, matured (cut) and assembled (along with the 5S RNA and 80 proteins) into ribosomes.

The number or gene dosage of these rRNA clusters in eukaryotic cells varies from as few as 100 to over 1500 copies per genome. Yeast has 140 copies, Neurospora has 200, Drosophilia has 240 and the human genome contains about 450. They are found as long repetitive units (the nucleolar organizer region) where as many as 500 copies of the entire cluster are repeated in tandem. In humans nucleolar organizers are found on the end of the short arms of chromosomes 13, 14, 15, 21, and 22.

Typical components of kits of the present invention include:

1.) PCR Master Mix
   a.) 10× Amplification Buffer
   b.) 2.5 mM dNTP mix (labeled or unlabeled)
   c.) two primers, wherein at least one primer is preferably labeled;
2.) DNA Polymerase;
3.) Restriction endonucleases; and
4.) Pre-packed G-50 columns.

In practicing the methods and utilizing the kits of the present invention, the following laboratory equipment may be required: automated sequencer, Thermal Cycler, Agarose Gel Electrophoresis Apparatus, Clinical Centrifuge and heating blocks or water baths.

The present invention will now be further illustrated with reference to the following Examples.

EXAMPLE 1

MRSA (methicillin resistant *Staphylococcus aureus*) isolates are identified at the hospital and delivered on typticase-soy agar slants. The patient name and hospital identification number are recorded and an isolate number is designated. Each number assigned has a three-letter prefix designating the hospital or origin (AMH, Archbold Memorial Hospital; TMH, Tallahassee Memorial Hospital) as well as a sequential numerical designation.

Five colonies from the slant are collected on a 5 millimeter bacterial inoculation loop and resuspended in 50 μl 10 mM EDTA in a microcentrifuge tube. The tube is boiled for 5 minutes and the resultant lysate, containing the DNA template, is used in a polymerase chain reaction (PCR). Although it is preferable to use a 5' end labeled primer from the 16S gene for prokaryotic typing, several alternative options are also available for strain typing. These include: (1) using a 5' end labeled primer from the 23S gene; (2) using both the 5' end labeled 16S and 23S primers; (3) using both 5' end labeled primers in conjunction with fluorescently labeled deoxynucleotide triphosphates (dNTPs); and/or (4) by using the labeled dNTPs alone in the PCR reaction.

PCR reaction mixture is prepared using 10 μl of a 10× Taq Amplification Buffer (50 μl 1 M Tris-HCl, pH 8.3; 250 μl 1 M Kcl; 20 μl 1 M MgCl$_2$; 2.25 μl NP-40; 2.25 μl Tween 20; 5 μl 1% gelatin; and 170.5 μl distilled water), 4 μl 2.5 mM dNTP mix (2.5 mM each dATP, dCTP, dGTP, dTTP), 100 ng fluorescently labeled 16S rRNA primer SEQ ID NO:8: (GTA CAC ACC GCC CGT), 100 ng nonlabeled 23S rRNA primer SEQ ID NO:11: (TCG CTC GCC GCT ACT), 1–10 μl of lysate from whole cells, 2.5 units AmpliTaq DNA polymerase, and sterile distilled water to bring the total volume to 100 μl. This mixture is overlayed with 100 μl mineral oil and placed in a Thermal Cycler (Perkin-Elmer, Norwalk, Conn.) under the following reaction conditions: 5 minute delay at 95° C., 35 cycles at 95° C. for 40 seconds, 50° C. for 25 seconds, 72° C. for 3 minutes; 10 minute delay at 72° C., followed by a 4° C. soak.

The PCR mixture is then separated from the oil overlay and 8 μl of the aqueous phase is mixed with 2 μl of a standard gel loading buffer. The aliquot is electrophoresed on a 2% agarose gel at 70 volts for one to two hours. The gel is stained with ethidium bromide and viewed under U-V illumination. The banding pattern reflects the rRNA gene cluster number of each bacterium. This initial pattern can be used as a preliminary test to distinguish between bacterial strains. If the banding patterns are very similar and more definitive results are desired, then the fingerprint is done on an automated sequencer.

Figure 11:
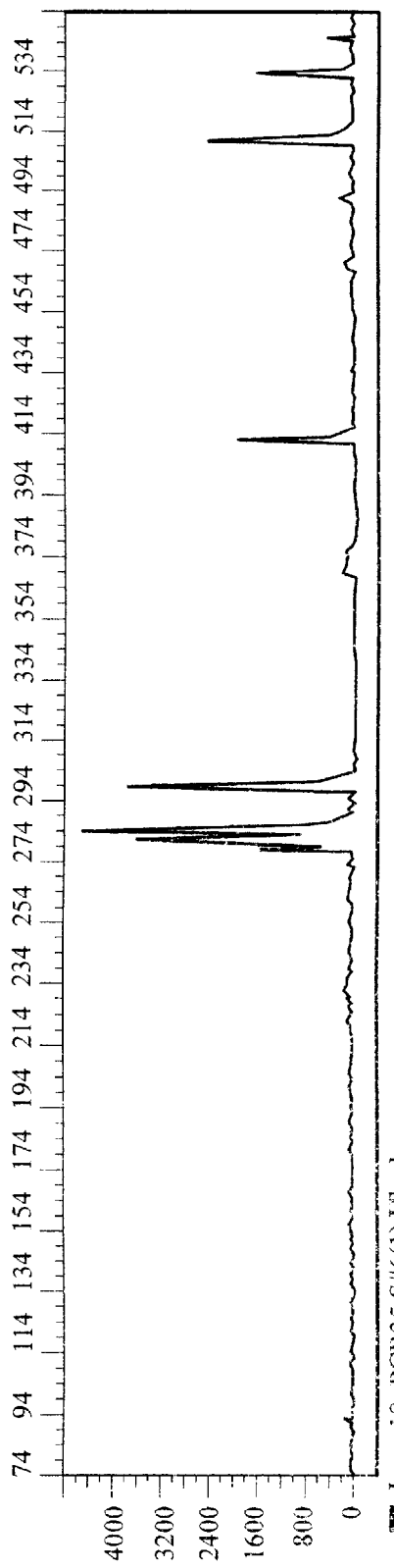
FIG. 11 is an electrophoretogram of MRSA sample #6(1) (HhaI)
Figure 12:
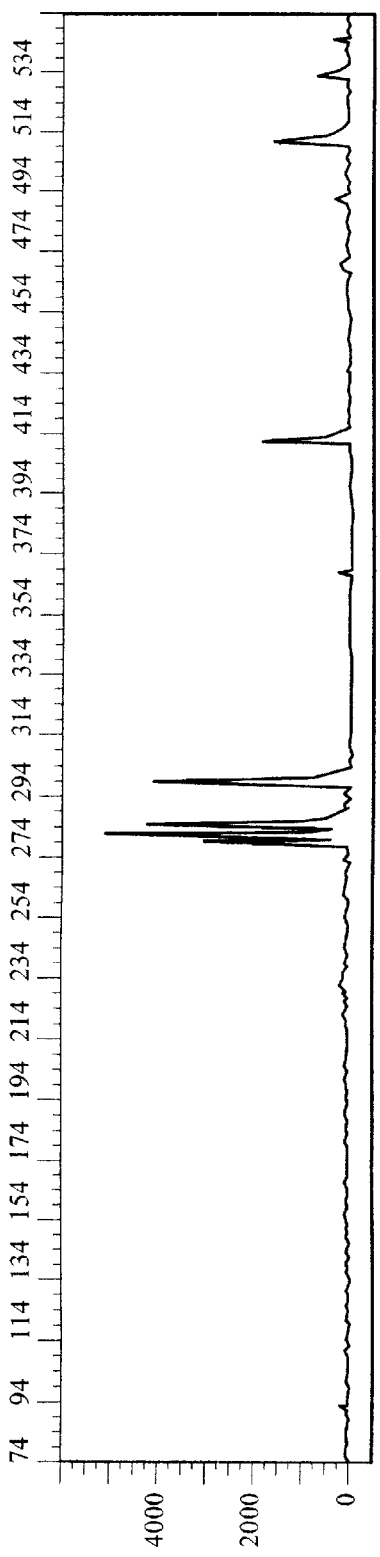
FIG. 12 is an electrophoretogram of MRSA sample #6-2B (HhaI)
Figure 13:
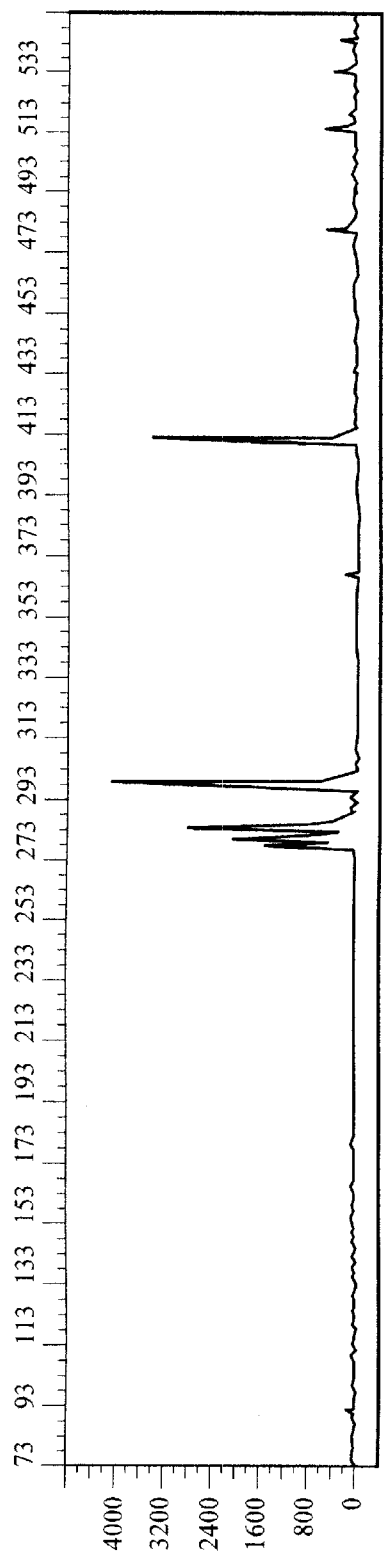
FIG. 13 is an electrophoretogram of MRSA sample #8 (HhaI)
Figure 14:
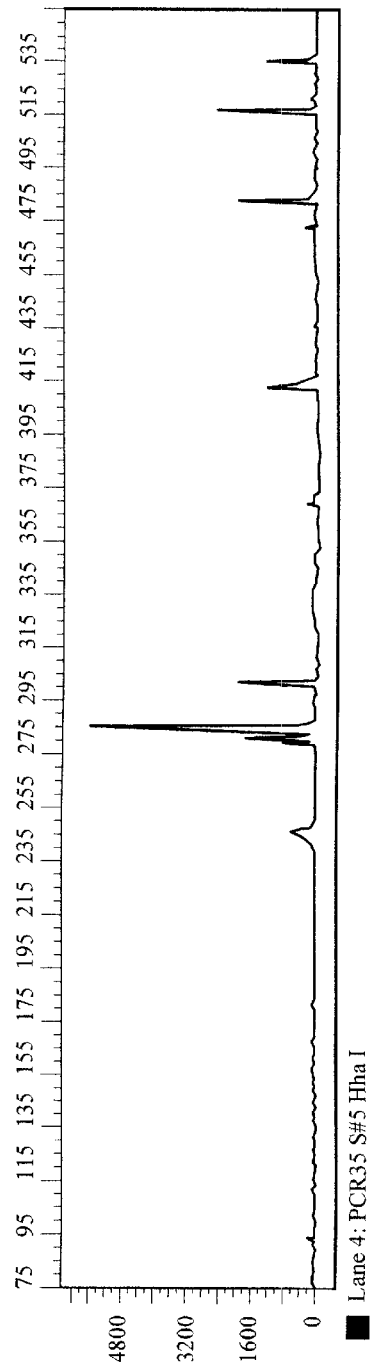
FIG. 14 is an electrophoretogram of MRSA sample #5 (HhaI)
Figure 15:
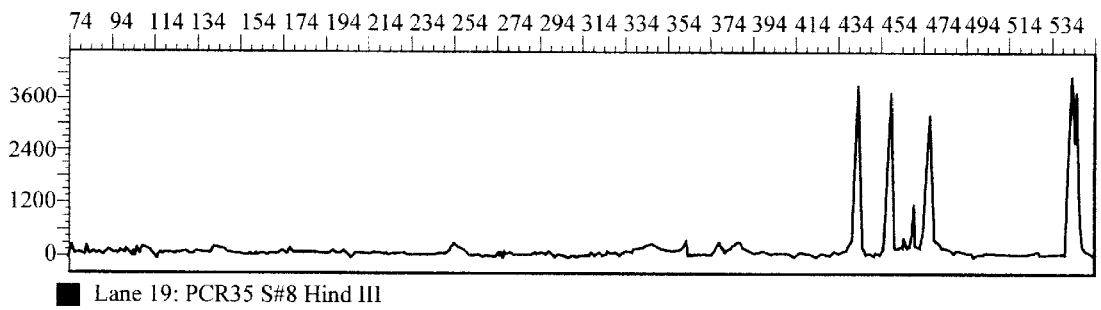
FIG. 15 is an electrophoretogram of MRSA sample #8 (HindIII)
Figure 16:
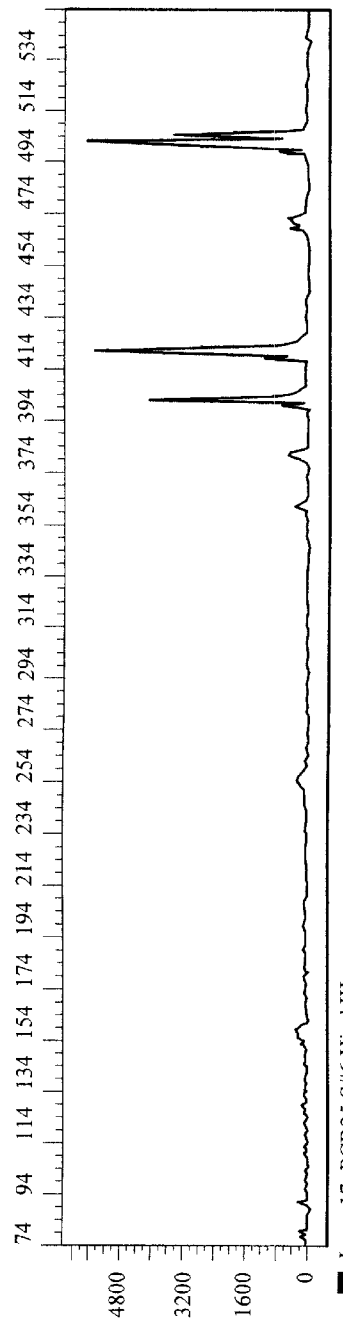
FIG. 16 is an electrophoretogram of MRSA sample #6 (HindIII).

The PCR mixture is passed through a G-50 column to remove unincorporated dNTPs and primers. The DNA concentration is determined on a minifluorometer. The PCR mixture then undergoes a 2-hour restriction digest with various four or six base endonucleases. HhaI and HindIII are generally preferred for restriction digests. However, other restriction endonucleases may prove to be more informative for other species. 100 ng of the amplified DNA product is added to a tube containing 1 μl React Buffer (Gibco BRL, Grand Island, N.Y.), and sterile distilled water to a volume of 9 μl. One microliter restriction endonuclease (HhaI or HindIII) is added and the mixture is incubated at 37° C. for a minimum of two hours. The entire restriction digest is dried in a SPEEDVAC™ Concentrator (Savant) and each is resuspended in a mixture of 4 μl deionized formamide and 0.5 μl GS2500P internal lane size standard (ABI, Foster City, Calif.). The samples are loaded onto a 6% polyacrylamide gel and electrophoresed on the 373A DNA Sequencing System (Applied Biosystems, Inc., Foster City, Calif.) under the Genescan software. The resulting DNA fingerprint is preserved in a gel file and can be printed onto paper as waveform patterns (electrophoretograms). See FIGS. 11–16.

EXAMPLE II

Eukaryotic Fingerprinting in the Ribosomal Gene Clusters

Figure 5:
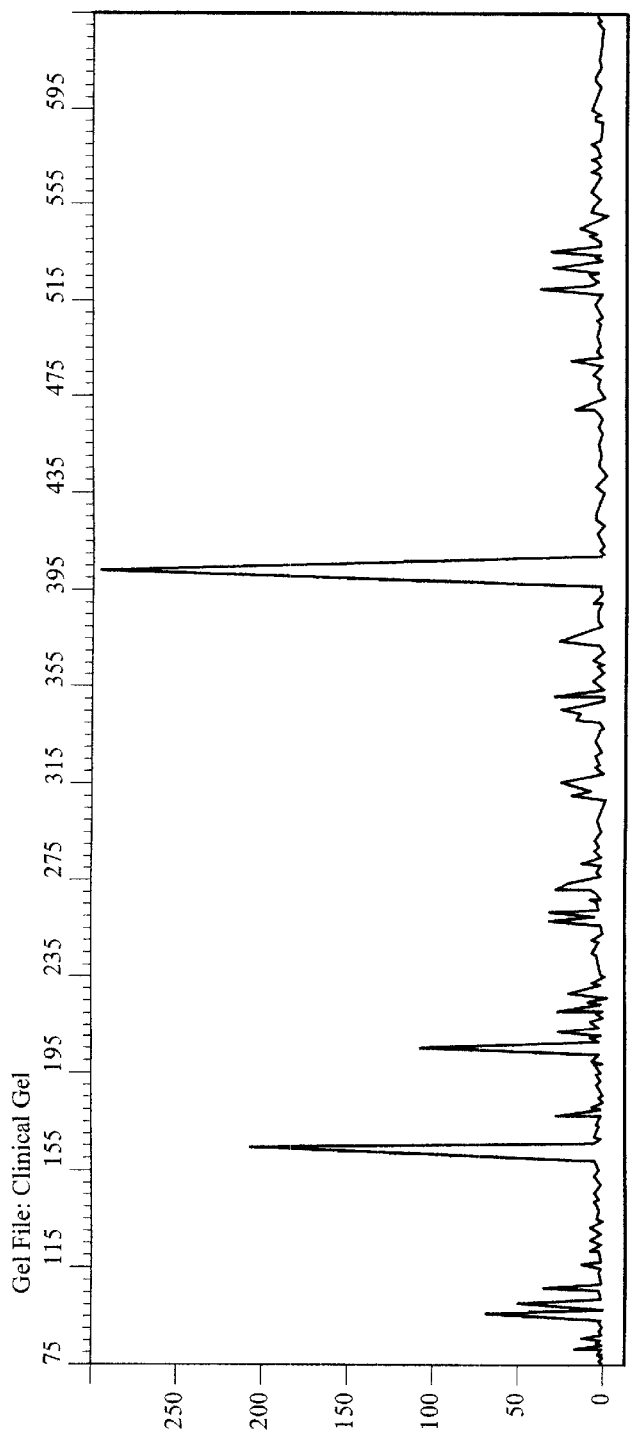
FIG. 5 is an electrophoretogram of the amplified intergene region of a horse (Daybreak Darling; TWH mare) depicted in lane four (4) in FIG. 4.
Figure 6:
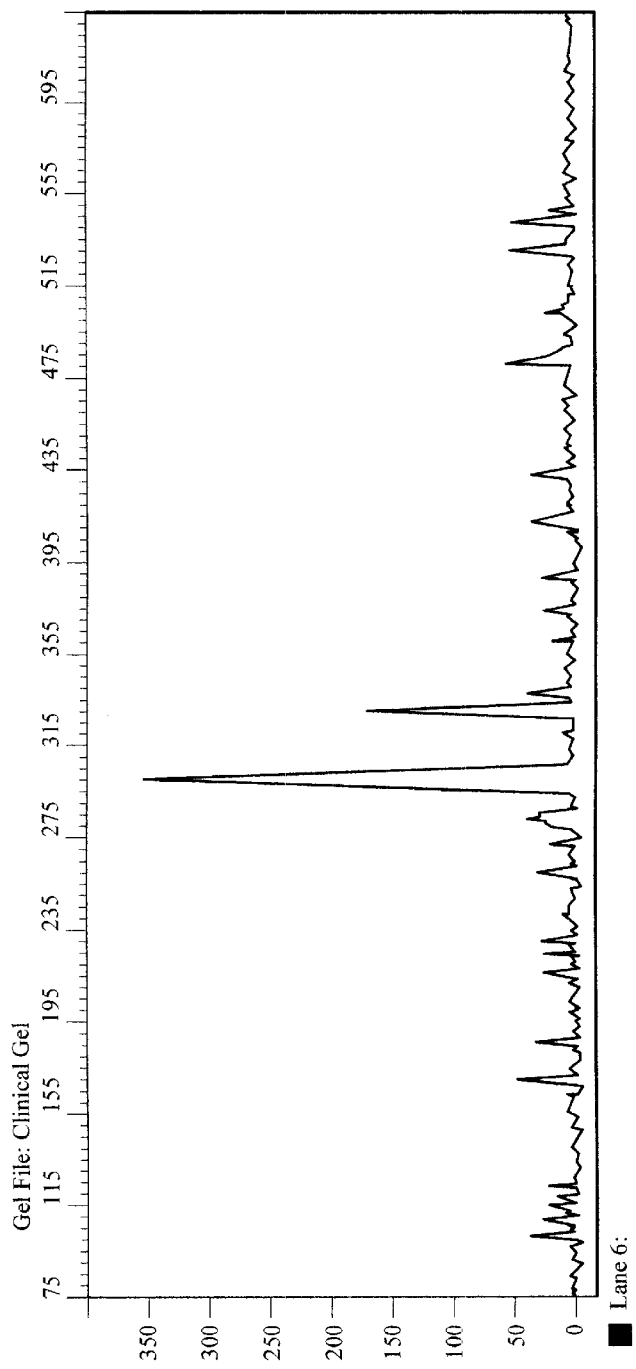
FIG. 6 is an electrophoretogram of the amplified intergene region of a horse (Bojangles; grade pony) depicted in lane 6 of FIG. 4.
Figure 7:
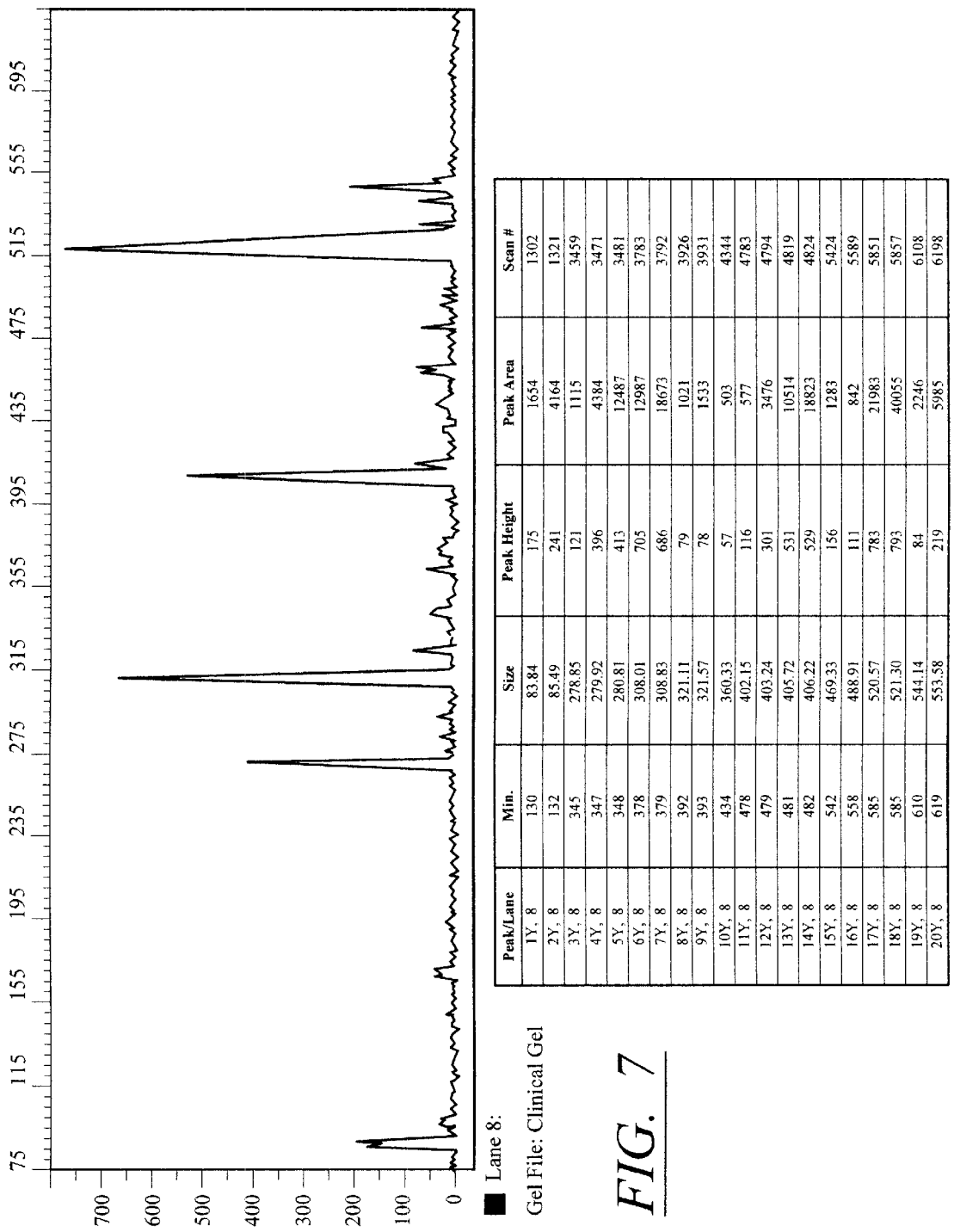
FIG. 7 is an electrophoretogram of the amplified intergene region of a cockroach (TaqI insect) depicted in lane 8 of FIG. 4.
Figure 8:
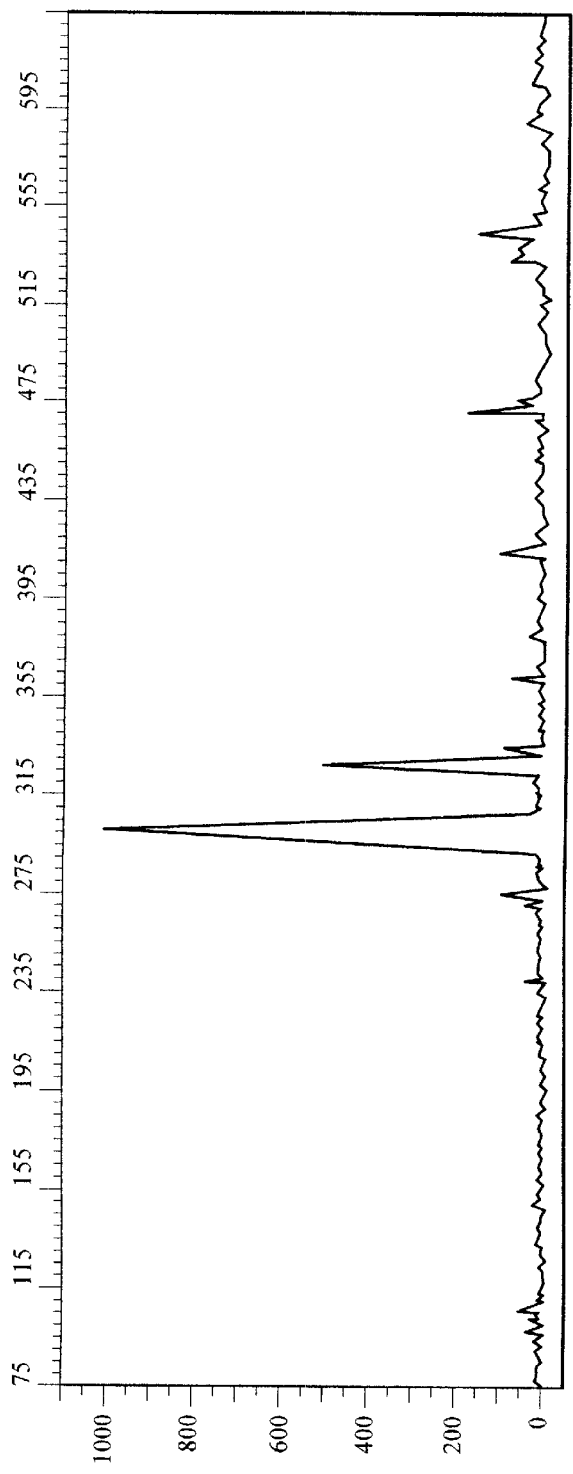
FIG. 8 is an electrophoretogram of the amplified intergene region of an Amphioxus (primitive worm) depicted in lane 7 of FIG. 4.
Figure 9:
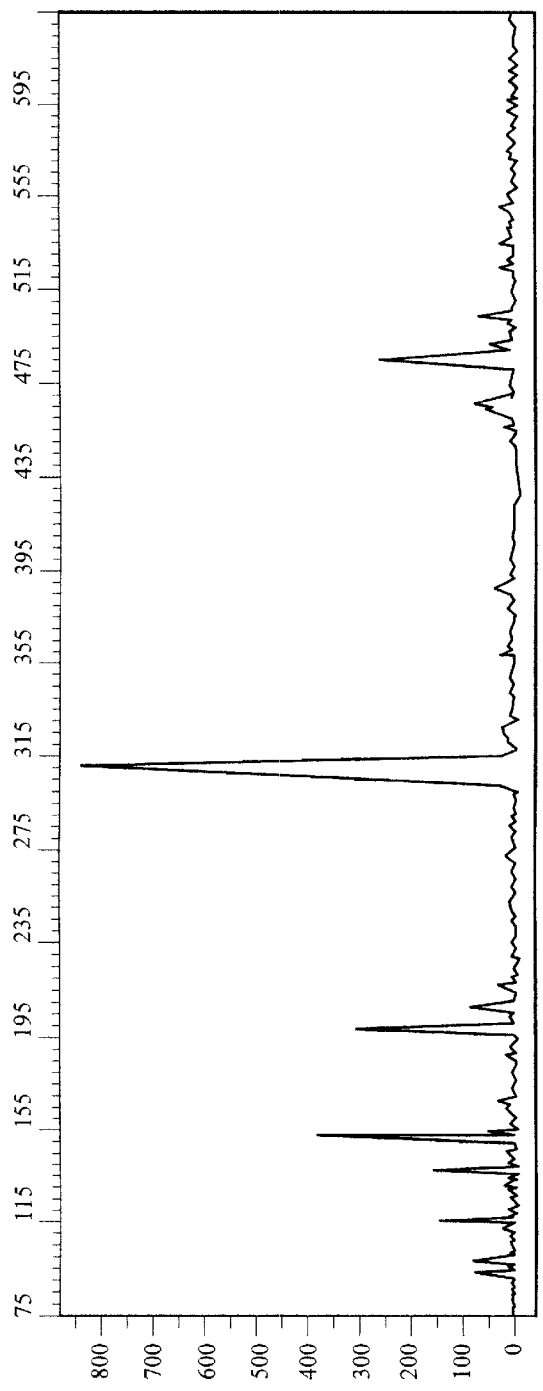
FIG. 9 is an electrophoretogram of a salamander (TaqI; amphibian) depicted in lane 12.

Fingerprint patterns of higher life forms have been created in accordance with Example II from the ribosomal gene clusters using the same priming sites as those used for prokaryotic (bacterial typing protocol. The priming sites for C—C and 7 are believed to be conserved in those organisms whose ribosomal intergene region amplified. These higher life forms included the horse, amphioxus (the first evolutionary organism to develop a notocord), cockroach (insect), sea urchin (echinoderm), salamander (amphibian), Rose Breasted Cockatoo (avian), rabbit (mammal), and human (mammal). As shown in FIG. 4, which is a photograph of an agarose gel, illustrates the PCR amplifications for the organisms used in our study. FIGS. 5–9 depict the waveform patterns for the horses in lanes 4 and 6, cockroach in lane 8, amphioxus in lane 7 and salamander in lane 11 of FIG. 4.

It is also believed that other higher life forms seem to have the primer 7 sequence conserved. These include *Physarum polycephalum* (slime mold), *Mucor racemosus* (dimorphic fungus), *Citrus limon* (lemon tree), *Mus musculus* (mouse), *Drosophila melanogaster* (fruitfly), *Tritrichomonas foetus* (protozoan), and *Homo sapien* (human). It is also believed that the primer 7 site is located in the 5' end of the 28S gene, rather than in the 5.8S gene as we previously believed. However, a small portion of the primer 7 sequence (approximately 6 bases) was found in the 3' end of the 5.8S sequence of *Tritrichomonas foetus*. Therefore, the amplified fragments presumably include a large and small band; the large band consisting of a small portion of the 18S gene (the priming site of C—C), internal transcribed spacer 1 (ITS1), the 5.8S RNA gene, internal transcribed spacer 2 (ITS2), and a small portion of the 28S RNA gene (the priming site of 7) while the smaller band contains the small portion of the 18S gene, ITS1, and most of the 5.8S gene.

The amplified DNAs from the above higher life forms were digested with HhaI and HindIII (the endonucleases used in the prokaryotic study), but found that these sites were relatively uninformative. Other restriction endonucleases which may prove to be better candidates for generating fingerprint patterns have been identified. For example, it is believed that the restriction endonucleases TaqI, SspI, NdeI, NdeII, and RsaI may enable one skilled in the art to identify individuals within a subspecies for possible linkage and pedigree studies. It is therefore believed that the selection of proper restriction endonucleases will enable those skilled in the art to identify individuals within a subspecies of higher life forms.

Data of the fingerprint patterns generated relative to the higher life forms is recited in FIGS. 4–9. This data was generated using fluroescent dUTP, rather than a labeled primer. In comparing the data between "Daybreak Darling TaqI" and "Bojangles TaqI," which concern two horses, a Tennessee Walking Horse and a grade pony, these two individuals seem to have unique fingerprint patterns, but further confirmation is believed to be needed.

The following constitutes a summary of the procedures utilized to generate the data relative to the higher life forms. A fresh deoxynucleotide triphosphate solution was prepared from stock and contained one-half the normal dTTP concentration. The final nucleotide concentrations within the dNTP solution were 25 mM each dGTP, dATP, and dCTP and 12.5 mM dTTP.

PCR was performed on blood samples by first treating the whole blood with GENERELEASER™ (Bioventures, Inc., Murfreesboro, Tenn.) as per manufacturer's protocol. PCR reaction mixture was then overlayed and PCR commenced. All other genomic DNA samples were kindly provided and previously prepared by Dr. deKloet and Gus Ray at Florida State University.

A polymerase chain reaction was prepared with approximately 50 ng template DNA, 10 µl 10× amplification buffer (50 µl 1 M Tris-HCl, pH 8.3; 250 µl M Kcl; 20 µl 1 M MgCl$_2$; 2.25 µl NP-40; 2.25 µl Tween 20; 5 µl 1% gelatin; and 170.5 µl distilled water), 4 µl of the prepared dNTP solution (final concentration 2.5 mM each dGTP, dATP, and dCTP and 1.25 mM dTTP), 1 µl of a 1:10 FluoroRed dilution (Rhodamine-4-dUTP, Amersham Life Sciences, Arlington Heights, Ill.), 0.5 µl each amplification primers, 2.5 units Amplitaq DNA polymerase (Perkin-Elmer, Norwalk, Conn.), and sterile distilled water to bring the total volume to 100 µl. PCR was carried out in a Thermal Cycler (Perkin-Elmer) under the following reaction conditions: 5 minute delay at 95° C.; 95° C. denaturation for 40 seconds, 50° C. annealing for 25 seconds, and 72° C. extension for 3 minutes for 30 cycles, followed by a 10 minute delay at 72° C.

The PCR mixture was then separated from the oil overlay and 8 µl of the aqueous phase was mixed with 2 µl of a standard gel loading buffer. The ail aliquot was electrophoresed on a 2% agarose gel at 70 volts for one to two hours. The gel was stained with ethidium bromide and viewed under U-V illumination. The PCR mixture was passed through a G-50 column to remove unincorporated dNTPs and primers and the DNA concentration was determined on a minifluorometer. The PCR mixture then underwent a 2-hour restriction digest with various four or six base endonucleases. It is believed that TaqI and SspI may prove to be the most informative for the higher life forms in this study; however, other restriction endonucleases may prove to be more informative for other species. 100 ng of the amplified DNA product was added to a tube containing 1 µl React Buffer (Gibco BRL, Grand Island, N.Y.) and sterile distilled water to a volume of 9 µl. One microliter restriction endonuclease (TaqI or SspI) was added and the mixture was incubated at 37° C. for a minimum of two hours. The entire restriction digest was dried in a SPEEDVAC™ Concentrator (Savant) and each was resuspended in a mixture of 4 µl deionized formamide and 0.5 µl GS2500P internal lane size standard (ABI, Foster City, Calif.). The samples were loaded onto a 6% polyacrylamide gel and electrophoresed on the 373A DNA Sequencing System (Applied Biosystems, Inc., Foster City, Calif.) under the Genescan software.

GENERELEASER (BioVentures, Inc., Murfreesboro, Tenn.), is a commercially available reagent which releases DNA from whole blood, tissues, and bacterial cultures while chelating, polymerase inhibitors released during cell lysis. GENERELEASER obviates genomic DNA purification and is claimed to improve amplification yield and specificity. It is provided as a ready to use stock and releases genomic DNA in ten minutes.

While the manufacturer's instructions call for 1 µl of whole blood, it is believed that by using 3 µl of whole blood, the yields are increased considerably. Therefore, 3µl whole blood is mixed with 20 µl GENERELESER in a 0.5 ml microfuge tube. The mix is overlayed with 100 µl mineral oil and the reaction is performed under the following conditions in a Thermocycler (Perkin Elmer, Norwalk, Conn.):

| | |
|---|---|
| 65° C. | 30 seconds |
| 8° C. | 30 seconds |
| 65° C. | 90 seconds |
| 97° C. | 180 seconds |
| 8° C. | 60 seconds |
| 65° C. | 180 seconds |
| 97° C. | 60 seconds |
| 65° C. | 60 seconds |
| 80° C. | hold. |

The amplification reagents are added under the oil without mixing the tube contents and amplification is executed as per our prokaryote protocol.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

Having described our invention, we claim:

1. A method of identifying a strain of a prokaryote or an individual of an eukaryote, said method comprising:

annealing ribosomal primers to two separate highly conserved regions of ribosomal DNA of the prokaryotic strain or the eukaryote, a highly variable region of DNA being spaced between the two highly conserved regions of DNA, said ribosomal primers being selected from the group consisting of AGA GTT TGA TCA/C TGG CTC SEQ ID NO:1:, AGA GTT TGA TCC TGG CTC SEQ ID NO:2:, CAG CCG CGG TAA TAC SEQ ID NO:3:, AAC AGG ATT AGA TAX CCT GG SEQ ID NO:4:, CAA AGG ATT TGA CGG SEQ ID NO:5:, TGG CTG TCG TCA GCT CGT GT SEQ ID NO:6:, GAC GTC AAG TCA TCA SEQ ID NO:7:, GTA CAC ACC GCC CGT SEQ ID NO:8:, AAG TCG TAA CAA GGT SEQ ID NO:9:, ATT AGC TAG TAG GTG SEQ ID NO:10:, TCG CTC GCC GCT ACT SEQ ID NO:11:, AGG GCA TCC ACC GTG SEQ ID NO:12:, ACT GGT TCA CTA TCG SEQ ID NO:13:, TCG GGG AGA ACC AGC TA SEQ ID NO:14:, CCA GTG AGC TAT TAC GC SEQ ID NO:15:, AGG AAT AAT AAC CTG TT SEQ ID NO:16:, CCA CCC TGT GTC GGT TT SEQ ID NO:17:, ATT TCG CTA CCT TAG SEQ ID NO:18:, TTT TAT CCG TTG AGC GA SEQ ID NO:19:, CTT AGA TGC TTT CAG C SEQ ID NO:20:, TGA CCC ATT ATA CAA AAG GT SEQ ID NO:21:, CCC AGT GGC AAC TCA SEQ ID NO:22:, CCC ATT GGC AAC TCA SEQ ID NO:23:, CCC ATA GGC AAC TCA SEQ ID NO:24:, CCC ATC GGC AAC TCA SEQ ID NO:25:, TGA GTT CGG GAT GGG SEQ ID NO:26:, TGA GTT CGG TAT GGG SEQ ID NO:27:, TGA GTT CGG AAT GGG SEQ ID NO:28:, TGA GTT CGG CAT GGG SEQ ID NO:29:, CTG TGT TCG GCA TGG SEQ ID NO:30:, and CTG TGT TCG ACA TGG ID NO:31:;

amplifying the highly variable region of ribosomal DNA to generate amplified DNA sequences having distributions in size and number;

labeling the amplified DNA sequences;

generating labeled DNA fragments from the labeled, amplified DNA sequences;

separating by electrophoresis the labeled DNA fragments to generate discrete bands, so that the prokaryotic strain or the eukaryotic individual can be identified generating a wave form pattern from the discrete bands; and identifying the prokaryotic strain or eukaryotic individual from generated wave form pattern.

2. The method of claim 1, wherein the prokaryotic strain or eukaryotic individual is a bacterium.

3. The method of claim 2, wherein the bacterium is *Staphylococcus aureus*.

4. The method of claim 3, wherein the *Staphylococcus aureus* is methicillin-resistant.

* * * * *

UNITED STATES PATENT AND TRADEMARK OFFICE
CERTIFICATE OF CORRECTION

PATENT NO.    : 6,395,475 B1
DATED         : October 30, 2001
INVENTOR(S)   : Leggett et al.

It is certified that error appears in the above-identified patent and that said Letters Patent is hereby corrected as shown below:

<u>Title page,</u>
Item [63], Related U.S. Application Data, replace "1994" with -- 1993 --.

Signed and Sealed this

Twenty-eighth Day of January, 2003

JAMES E. ROGAN
*Director of the United States Patent and Trademark Office*

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

AGAGTTTGAT CATGGCTC                                                      18

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AGAGTTTGAT CCTGGCTC                                                      18

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CAGCCGCGGT AATAC                                                         15

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AACAGGATTA GATACCCTGG                                                    20

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CAAAGGAATT GACGG                                                    15

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TGGCTGTCGT CAGCTCGTGT                                               20

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GACGTCAAGT CATCA                                                    15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTACACACCG CCCGT                                                    15

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AAGTCGTAAC AAGGT                                                    15

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATTAGCTAGT AGGTG                                                    15
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TCGCTCGCCG CTACT                                                        15

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGGGCATCCA CCGTG                                                        15

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

ACTGGTTCAC TATCG                                                        15

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TCGGGGAGAA CCAGCTA                                                      17

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CCAGTGAGCT ATTACGC                                                      17

(2) INFORMATION FOR SEQ ID NO:16:

(i) SEQUENCE CHARACTERISTICS:
        (A) LENGTH: 17 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

AGGAATATTA ACCTGTT                                                          17

(2) INFORMATION FOR SEQ ID NO:17:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

CCACCCTGTG TCGGTTT                                                          17

(2) INFORMATION FOR SEQ ID NO:18:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

ATTTCGCTAC CTTAG                                                            15

(2) INFORMATION FOR SEQ ID NO:19:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

TTTTATCCGT TGAGCGA                                                          17

(2) INFORMATION FOR SEQ ID NO:20:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

CTTAGATGCT TTCAGC                                                           16

(2) INFORMATION FOR SEQ ID NO:21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

TGACCCATTA TACAAAAGGT                                                        20

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CCCATGGGCA ACTCA                                                             15

(2) INFORMATION FOR SEQ ID NO:23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CCCATTGGCA ACTCA                                                             15

(2) INFORMATION FOR SEQ ID NO:24:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CCCATAGGCA ACTCA                                                             15

(2) INFORMATION FOR SEQ ID NO:25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CCCATCGGCA ACTCA                                                             15

(2) INFORMATION FOR SEQ ID NO:26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
TGAGTTCGGG ATGGG                                          15

(2) INFORMATION FOR SEQ ID NO:27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TGAGTTCGGT ATGGG                                          15

(2) INFORMATION FOR SEQ ID NO:28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TGAGTTCGGA ATGGG                                          15

(2) INFORMATION FOR SEQ ID NO:29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

TGAGTTCGGC ATGGG                                          15

(2) INFORMATION FOR SEQ ID NO:30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CTGTGTTCGG CATGG                                          15

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CTGTGTTCGA CATGG                                          15
```